United States Patent
Goralczyk et al.

(10) Patent No.: US 10,653,613 B2
(45) Date of Patent: *May 19, 2020

(54) COMPOSITIONS COMPRISING LYSOZYME HYDROLYSATE FOR USE IN KERATIN-CONTAINING TISSUE

(71) Applicant: DSM IP ASSETS B.V., Heerlen (NL)

(72) Inventors: Regina Goralczyk, Kaiseraugst (CH); Hasan Mohajeri, Kaiseraugst (CH); Jonas Wittwer Schegg, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/104,813

(22) PCT Filed: Nov. 28, 2014

(86) PCT No.: PCT/EP2014/075934
§ 371 (c)(1),
(2) Date: Jun. 15, 2016

(87) PCT Pub. No.: WO2015/090906
PCT Pub. Date: Jun. 25, 2015

(65) Prior Publication Data
US 2016/0317429 A1 Nov. 3, 2016

Related U.S. Application Data

(60) Provisional application No. 61/917,668, filed on Dec. 18, 2013.

(51) Int. Cl.
| | |
|---|---|
| *A61K 8/96* | (2006.01) |
| *A61K 38/01* | (2006.01) |
| *A61Q 19/00* | (2006.01) |
| *A61Q 3/00* | (2006.01) |
| *A61Q 5/00* | (2006.01) |
| *A61K 8/66* | (2006.01) |
| *A61K 38/05* | (2006.01) |
| *A61K 38/06* | (2006.01) |
| *A61Q 17/04* | (2006.01) |

(52) U.S. Cl.
CPC ............ *A61K 8/96* (2013.01); *A61K 8/66* (2013.01); *A61K 38/01* (2013.01); *A61K 38/05* (2013.01); *A61K 38/06* (2013.01); *A61Q 3/00* (2013.01); *A61Q 5/00* (2013.01); *A61Q 5/002* (2013.01); *A61Q 19/00* (2013.01); *A61K 2800/74* (2013.01); *A61K 2800/92* (2013.01); *A61Q 17/04* (2013.01)

(58) Field of Classification Search
CPC ..................................................... C12N 9/2462
See application file for complete search history.

(56) References Cited

U.S. PATENT DOCUMENTS

| | | | | |
|---|---|---|---|---|
| 6,183,742 | B1 * | 2/2001 | Kiczka | A61K 38/47 424/94.61 |
| 8,232,243 | B2 * | 7/2012 | Moosmann | A61K 38/04 514/1.9 |
| 9,516,893 | B2 * | 12/2016 | Gibson | A23L 33/175 |
| 2008/0213242 | A1 * | 9/2008 | Ferrari | A61K 38/47 424/94.61 |
| 2009/0029005 | A1 | 1/2009 | Van Amerongen et al. | |
| 2011/0086803 | A1 * | 4/2011 | De Roos | C12P 13/22 514/17.5 |

FOREIGN PATENT DOCUMENTS

| | | |
|---|---|---|
| DE | 3501560 | 7/1986 |
| WO | WO 96/21463 | 7/1996 |
| WO | 2008/052995 | 5/2008 |
| WO | 2009/128713 | 10/2009 |
| WO | 2009/133055 | 11/2009 |
| WO | 2014/068499 | 5/2014 |

OTHER PUBLICATIONS

Jackson-Cannady ("Sunscreen: Are You Really Covered? What's true, and what's not, about sunscreen and SPF." www.webmd.com Nov. 27, 2012).*
International Search Report and Written Opinion of the ISA for PCT/EP2014/075934, dated Jan. 12, 2015, 11 pages.
"Use of lysozyme dimer for treating or preventing cancer—hair growth disorders and diseases of fish and bees, acts as non-specific immune stimulant", Thomson Scientific, Oct. 31, 1997, 3 pages.
International Preliminary Report on Patentability dated Jun. 30, 2016.

* cited by examiner

*Primary Examiner* — Christina Bradley
(74) *Attorney, Agent, or Firm* — Nixon & Vanderhye P.C.

(57) ABSTRACT

Trp-containing peptides, preferably from hen's egg hydrolysate can increase the Cys levels in blood serum. This results in increased keratin production, and enhances growth, appearance, and/or volume in keratin-containing tissue including skin, hair, and/or nails.

3 Claims, 15 Drawing Sheets

Figure 6

DSM Nutritional Products 
Product Data Sheet lumiVida™

Description lumiVida™ is a protein hydolysate derived from an egg white protein. It contains a guaranteed minimum quantity of bioactive Tryptophan-containing peptides in a controlled ratio to large neutral amino acids (LNAA). The controlled Trp:LNAA ratio assures high uptake of Trp into the brain.

Product identification
Product code: xxx

Specifications

| | |
|---|---|
| Appearance: | powder |
| Colour: | white to light yellow |
| Protein (on anhydrous material) | >= 80% |
| Trp (mass% of protein) | >= 6.5% |
| Tyr (mass% of protein) | >= 3.5% |
| Ratio Trp/LNAA (molar) | 0.18 – 0.20 |
| Moisture | < 5.0% |
| Ash | < 10% |
| Sodium | < 6% |

Microbiological purity:

- Total aerobic microbial count — $< 10^3$ CFU/g
- Total combined yeasts/moulds count — $< 10^2$ CFU/g
- Enterobacteria — < 10 CFU/g
- Salmonella spp — negative in 25 g
- Escherichia coli — negative in 10g
- Staphylococcus aureus — negative in 10g
- Pseudomonas aeruginosa — negative in 10g

Stability and storage lumiVida™ maintains its declared protein content for at least 24 months from the date of manufacture when stored in the unopened original container and at a temperature below 25°C. The 'best used before' date is printed on the label.

Applications

Especially suited for food applications and dietary supplements lumiVida

Intact lysozyme lumiVida

Intact lysozyme lumiVida

Intact lysozyme lumiVida

Intact lysozyme

COMPOSITIONS COMPRISING LYSOZYME HYDROLYSATE FOR USE IN KERATIN-CONTAINING TISSUE

This application is the U.S. national phase of International Application No. PCT/EP2014/075934 filed 28 Nov. 2014, which designated the U.S. and claims the benefit of U.S. Provisional Application No. 61/917,668 filed 18 Dec. 2013, the entire contents of each of which are hereby incorporated by reference.

This invention relates to the use of an oral formulation of peptides which contain the amino acid tryptophan ("Trp") to benefit the production and maintenance of skin tissues, hair and nails. The peptides act by increasing the concentration of a different amino acid, cysteine ("Cys") as well as cysteine and glutathione in the blood. Cys is required for the synthesis of keratin, a key component in the synthesis of skin, hair and nails. It also involves the use of the peptides to increase glutathione in the serum as well. This invention also relates to nutritional supplements, foods and other formulations which provide a skin- hair- and/or nail-benefitting amount of TRP-containing peptides.

BACKGROUND OF THE INVENTION

Keratin is a family of fibrous structural proteins, and is the key structural material making up the outer layer of skin and also the hair and nails. Keratin proteins contain a large amount of cysteine (Cys) (approximately 14%). As keratinized cells are constantly being shed and replaced, it is important that the body have a large pool of bioavailable Cys for protein synthesis.

Cys is considered a non-essential amino acid, but in some cases, such as in infants, the elderly, and individuals with certain metabolic diseases or malabsorption syndrome, it may be considered essential. It is readily available in many high protein foods, including meats, but this may be problematic for those who do not consume meat. In some regions it can be added as a food additive (E number is E920). However, such additives are generally not favored by consumers, and many regulatory agencies either limit or do not allow amino acids to be added to food.

A hydrolyzed hen's egg lysozyme is described in WO 2008/052995 (DSM IP ASSETS BV; which is hereby incorporated herein by reference) which has a Trp/Large Neutral Amino Acid ("LNAA") ratio of more than 0.15, wherein LNAAs are the sum of the phenylalanine, leucine, isoleucine and valine in the plasma. Many of the hydrolyzed peptides are di- or tri-peptides containing Trp. A commercial product form of this lysozyme hydrolysate is available from DSM Nutritional Products under the name "LumiVida". The lysozyme hydrolysate has been shown to be beneficial for a number of aspects including improving mood and cognition.

It would be desirable to make Cys which has been ingested more bioavailable in order to benefit keratin containing tissues, such as the skin, nails, and hair.

DESCRIPTION OF THE FIGURES

FIG. 6 is the data sheet of LUMIVIDA

DETAILED DESCRIPTION OF THE INVENTION

Figure 1:
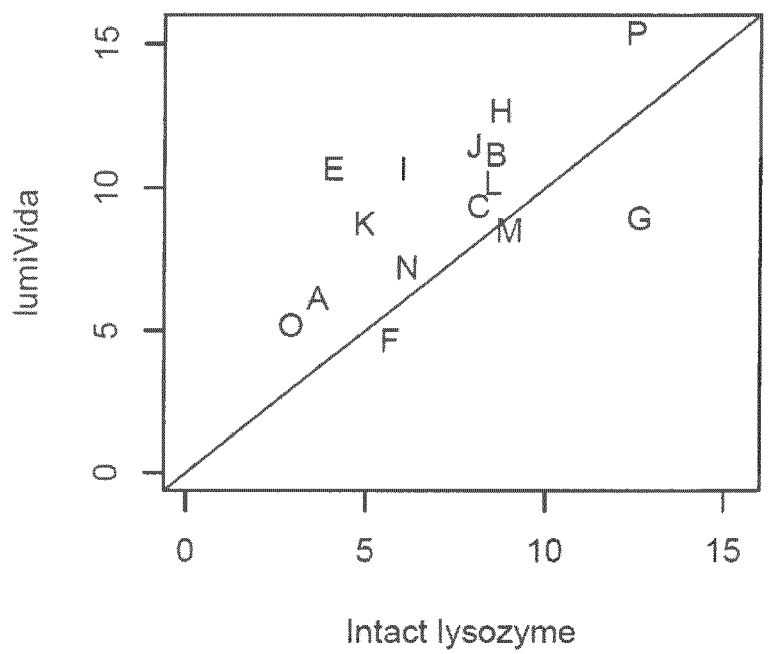
FIG. 1 is a graph which shows the individual dAUC values after lumiVida consumption versus intact lysozyme intake. Points on the diagonal correspond to equal values in both. Points above the diagonal represent individuals with higher response for lumiVida™ than for intact lysozyme. Overall, the dAUC after lumiVida supplementation was significantly higher than after intact lysozyme ingestion (Wilcoxon test, p=0.0067).

It has been found, in accordance with this invention, that a hydrolysate of hens egg lysozyme comprising peptides containing Trp- has the beneficial property of increasing the bioavailability of cysteine. This effect was not observed using intact hens egg lysozyme. Thus this invention relates to a method of increasing the amount of Cys in blood serum comprising administering a hens egg lysozyme hydrolysate comprising peptides containing Trp. As Cys levels increase in the blood, various subsequent advantages are realized, and these also form some embodiments of this invention.

Another finding of this invention is that hens egg lysozyme hydrolysate can also increase glutathione ("Glu") levels. Thus, another embodiment of this invention is the use of hens egg lysozyme to increase glutathione levels in at least one tissue.

In preferred embodiments, the peptides containing Trp are di- and/or tri-peptides such as those found in commercial lysozyme hydrolysates such as LUMIVIDA® from DSM Nutritional Products, Switzerland.

Increasing Cys Levels in the Blood

One embodiment of this invention is the use of lysozyme hydrolysate to increase the amount of cysteine in the body. Cystine is an amino acid formed by the oxidation of two cysteine (Cys) molecules that covalently link via a disulfide bond. Human hair and skin contain approximately 10-14% cysteine by mass. Cystine is converted to Cys rapidly. Because of the ease of the cystine to Cys (and reverse) reaction, the nutritional benefits of cystine are the same as Cys. Further, cystine serves as a substrate for the cystine-glutamate antiporter. This transport system, which is highly specific for Cys and glutamate is used to increase the concentration of cystine inside the cell. The anionic form of cystine is quickly reduced to Cys. Cys prodrugs (for example acetylcysteine) increase glutamate release into the extracellular space.

Thus, another aspect of this invention is the administration of the lysozyme hydrolysate to a person desirous of increasing cystine concentration in at least one tissue, or to achieve at least one of the benefits of increasing cysteine which are disclosed herein.

Thus, the lysozyme hydrolysate of this invention, by increasing levels of L-cysteine, has other effects throughout the body. For example can help reduce the effects of allergies, acne, sun-damaged skin, chronic bronchitis and emphysema. For allergic reactions which result in the production of phlegm, the presence of cysteine can break the bonds that cause the collagen in the mucus to clump; secretions are runnier and thus easier to expel.

The lysozyme hydrolysate of this invention helps protect against skin damage by the sun. Cysteine helps to form enzymes which maintain the activity of the p53. The p53 pathway initiates a series of events resulting in a potentially cancerous cell to undergo apoptosis. Cysteine also is important for the formation of caspases, which breaks down dead cells.

The lysozyme hydrolysate of this invention is also useful in the treatment of or amelioration of acne, preferably together with vitamin B5 (pantothenic acid). Cysteine helps the body absorb vitamin B5.

Thus, another aspect of this invention is the administration of the lysozyme hydrolysate to a person desirous of increasing cystine concentration in their hair and/or skin, or to achieve the aforementioned benefits of increasing cystine.

Keratin Production

As Cys is an amino acid which is key in the manufacture of the protein keratin, another aspect of this invention is a method of enhancing keratin production by providing a keratin-enhancing-effective amount of hens egg lysozyme hydrolysate comprising Trp-containing di-and tri- peptides to a person desirous of enhancing the appearance of his/her hair, skin, cuticle, nails or other keratin-containing tissue, or for someone suffering from an adverse health condition due to the lack of sufficient keratin for example because of mutations in the genes encoding keratin. Another embodiment of this invention is the use of hen egg lysozyme hydrolysate to enhance the manufacture of keratin, and thereby enhance the appearance of skin, hair, cuticles, nails or other keratin-containing tissue. Another embodiment of this invention is the use of hen egg hydrolysate to make a pharmaceutical or nutraceutical for the enhancement of the manufacture of keratin in a person experiencing a keratin deficiency, such as in skin fragility disorders or Steatocystoma multiplex (a benign, autosomal dominant congenital condition resulting in multiple cysts on a person's body).

Enhancing the Appearance of Keratin Containing Structures

Another aspect of this invention is a method of enhancing the appearance of hair, skin, cuticles and/or nails comprising providing a hair- skin- cuticle- or nail-enhancing effective amount of hens egg lysozyme hydrolysate comprising Trp-containing di-and tri- peptides to a person desirous of enhancing the appearance of his/her hair, skin, cuticles, or nails.

This invention also relates to the use of hens egg lysozyme hydrolysate comprising Trp-containing di-and tri- peptides to a person desirous of enhancing the appearance of his/her hair, skin, cuticles or nails. It also related to the use of hens egg lysozyme hydrolysate comprising Trp-containing di-and tri- peptides for enhancing the production of keratin. It is also directed to the non-therapeutic use of a hens egg lysozyme hydrolysate in the manufacture of a pharmaceutical, nutraceutical, food or food supplement which increases the amount of Cys in the blood serum, enhances keratin biosynthesis, or enhances the appearance of hair, skin or nails.

Increase Glutathione

Another aspect of this invention is the use of the above described lysozyme hydrolysate to increase glutathione concentrations. It also relates to increasing levels of glutathione in the blood by ingesting the aforementioned hens egg lysozyme hydrolysate. L-cysteine is a basic building block for glutathione, one of the body's most important antioxidants. Glutathione has a number of functions, including protecting DNA from oxidative damage, detoxifying heavy metals, cardiovascular system support (especially arthrosclerosis), various cancers, and immune system support. It also functions by repleting vitamins C and E as they perform antioxidant functions.

The increased glutathione availability thus means that various groups of people can benefit from using lysozyme hydrolysate, including:

Those wishing to improve muscle mass—for example body builders and other fitness enthusiasts as well as those who are experiencing muscle wasting (such as sarcopenia). Muscle wasting often accompanies other conditions/illnesses where the patient loses muscle mass due to immobility for an extended period of time (i.e. more than approximately 2 weeks).

Those wishing to improve digestion, as glutathione is known to protect the stomach lining.

Kits

Another aspect of this invention is a method of marketing a lysozyme hydrolysate comprising providing a kit comprising:
 a) multiple dosages of lysozyme hydrolysate; and
 b) information which informs a consumer of the health benefits of said lysozyme hydrolysate selected from the group consisting of:
   benefits to hair, benefits to skin, benefits to nails, benefits to acne, benefits to chronic bronchitis and/or emphysema, benefits for detoxifying heavy metals, benefits to arthrosclerosis, benefits to deficiencies of vitamins A or C, and benefits to muscle mass.
 c) optional further information selected from the group consisting of:
   dosage regimes, expiration dates, and additional benefits not mentioned in b).

Dosage
Dosages

The dosages for increasing cysteine, cysteine and/or glutathione in the blood should be at least 0.5 grams hydrolysate per day for an adult, and may extend up to large dosages, such as over 10 grams per day. The preferred amount is from 0.5 grams to about 7.5 grams hydrolysate per day, preferably from about 1 gram to about 6 grams per day.

The protein hydrolysate is consumed once or twice per day to achieve acute effects. In another preferred embodiment the protein hydrolysate is consumed 2× per day, with an interval of at least 6 hours between doses, and preferably no more than 18 hours between doses. In more preferred embodiments, the doses are consumed at approximately 12 hour intervals, such as early morning and early evening. Additional dosings per day may also be consumed if desired, such as 2-8 grams Trp-containing protein hydrolysate per day, and these dosings may be seen to have additional benefits. Another dosage is up to 6 grams per day. Another dosage is up to 8 grams per day. Another dosage is less than 6 grams per day, but at least 1 gram per day. Dosings of 1-3 grams per day are also envisioned. Dosings of greater than 10 grams Trp-containing protein hydrolysate per day are also effective, but are not preferred as there may be taste issues.

In another embodiment, this dosage form may also be administered multiple times per day for an extended period of time, such that the person receives 10-100mg Trp per day, preferably 25-70 mg Trp per day. In one preferred embodiment, the person receives 1 gram of hydrolysate per day, which contains a total of 62-64 mg Trp. In another preferred embodiment, the person receives 0.5 grams of Trp-hydrolysate per day, which contains a total of 20-26 mg Trp. In another embodiment, the person receives multiples of these dosages so that the total amount of Trp per day is between 25-1000 mg, preferably 50-800 mg, and more preferably 60-600 mg.

In addition to daily beauty care routine, hair and nails should also be supplied with the right nutrients to keep strong and healthy. Healthy hair is naturally shiny and strong. Nutrients in the hair follicles and bulb are necessary for the development and growth of healthy hair, and for a strong hair structure, shine, color and elasticity. Healthy hair growth requires a wide variety of micronutrients and vitamins. Hair reflects the overall condition of the body and nutritional deficiencies.

Strong nails also require proper micronutrients. Soft or brittle fingernails can reveal nutritional deficiencies before symptoms in the body appear. Nails are made from a protein, keratin, and grow continuously, so a continuous supply of the right ingredients from inside supports the nail structure and promotes the growth of attractive, strong nails.

Beautiful hair is naturally full, strong and shiny. Hair health depends on blood supply, circulation, hormones, stress levels and nutrition. A strong hair texture requires essential nutrients to support the growth of cells in the hair roots and provide hair full of vigor and vitality. Hair-building materials, such as vitamins and other micronutrients, support the biological processes that provide for the maintenance of a strong hair texture and shine, firmness and elasticity of the hair.

Keratin is a major structural component of skin, hair and nails. Keratin filaments are abundant in keratinocytes in the cornified layer of the epidermis; these are cells which have undergone keratinization. In addition, keratin filaments are present in epithelial cells in general. Keratins, also described as cytokeratins are polymers of type I and type II intermediate filaments. The keratin molecule is held together by intra- and intermolecular hydrogen bonds. In addition, keratins have large amounts of the sulfur-containing amino acid cysteine, required for the disulfide bridges that confer additional strength and rigidity by permanent, thermally-stable bonds. The more flexible and elastic keratins of hair have fewer interchain disulfide bridges than the keratins in mammalian fingernails.

Human hair is approximately 14% cysteine. Hair and other α-keratins consist of a-helically-coiled single protein strands (with regular intra-chain H-bonding), which are then further twisted into superhelical ropes that may be further coiled. The sulfur-containing amino acid cysteine occurs naturally in foods and can also be manufactured by the body from the amino acid methionine.

In the production of cysteine, methionine is converted to S-adenosyl methionine (SAM), which is then converted to homocysteine. Homocysteine then reacts with serine to form cysteine.

Daily Recommended Intake (DRI)*
 all individuals 1 year of age or greater to consume 25 milligrams of cysteine plus methionine (combined) for every 1 gram of food protein.

Recommendation for each age and gender group, assuming RDA-level protein intake and 50% of sulfur-containing amino acid needs supplied by cysteine:
 Children 1-3 years: 163 mg of cysteine
 Children 4-8 years: 238 mg of cysteine
 Males 9-13 years: 425 mg of cysteine
 Males 14-18 years: 650 mg of cysteine
 Males 19 years and older: 700 mg of cysteine
 Females 9-13 years: 425 mg of cysteine
 Females 14 years and older: 575 mg of cysteine Pregnant or lactating females: 888 mg of cysteine The protein hydrolysate of this invention can substitute for various natural sources of cysteine, including these:

| Food | g Cysteine per 100 g | g Cysteine per portion |
| --- | --- | --- |
| Egg, whole | 0.272 | 0.136 (~50 g) |
| Egg white | 0.287 | 0.095 (~33 g) |
| Egg yolk | 0.264 | 0.045 (~17 g) |
| Milk whole full fat | 0.030 | 0.073 (~240 ml) |
| Yoghurt | 0.032 | 0.036 (~113 g) |
| Chicken meat meat only, cooked, fried | 0.393 | 1.014 (~258 g, bone and skin removed) |
| Oats | 0.408 | 0.163 (40 g) |
| Brussel sprouts cooked, boiled, drained, without salt | 0.016 | 0.012 (78 g) |
| Broccoli cooked, boiled, drained, without salt | 0.031 | 0.024 |

Bioactive peptides in the egg lysozyme hydrolysate according to this invention deliver highly bioavailable amino acids to nourish skin, hair and nails. A high cysteine content in egg lysozyme hydrolysate according to this invention (6.2%) delivers building blocks for keratin, the key structural component of the skin, hair and nails. Thus, the egg lysozyme hydrolysate according to this invention can serve as a valuable dietary source to meet daily recommended intakes. This is especially valuable for dieters and vegetarians who lack significant sources for cysteine.

2g of egg lysozyme hydrolysate according to this invention provides 13% of the DRI for cysteine.

Cysteine from egg lysozyme hydrolysate according to this invention is bioavailable. There is a consumer need for cysteine supplements, especially for vegetarians:

"I am vegetarian and don't eat animal products. Since I have to control my diet every day to stay slim. I was always looking for a product that helps me getting enough nutrients to keep my skin healthy and my hair and shiny".

Thus another embodiment of this invention is the use of lysozyme hydrolysate for vegetarians who ingest egg based products for the various benefits disclosed herein, such as increasing cysteine and glutathione levels, and enhancing the appearance of skin, nails, and/or hair. Another aspect of this invention is a method of supplementing the diet of an egg-ingesting vegetarian in need of cysteine enhancement comprising administering egg lysozyme hydrolysate.

The following non-limiting examples are presented to further illustrate the invention.

EXAMPLE 1

Clincial Trial

Rationale:

lumiVida™ is a hydrolysed form of lysozyme, a protein from hen egg. It has been shown that lumiVida™ has mood improving properties due to the fact that it is rich in tryptophan (Trp), an amino acid that is a substrate for serotonin synthesis. In the current study, we wished to compare intact and hydrolysed lysozyme in terms of plasma levels of Trp, (and the other members from the class of large neutral amino acids. LNAA) in humans over a four-hour postprandial period. In addition, the amino acids cysteine, the di-amino acid, cystine that is formed by the oxidation of two cysteine resulting in a disulfide bridge and the cysteine-containing tripeptide glutathione were investigated over the same period of time in subjects consuming either lumiVida™ or intact lysozyme.

Objective:

To assess the time kinetics of plasma Trp/LNAA ratios following a single treatment of (1) lumiVida™, (2) intact lysozyme, or (3) a 30/70 mol percent Trp mixture of lumiVida™ and intact lysozyme.

To also assess plasma kinetics of cysteine, cystine and glutathione after consumption of either lumiVida™ or intact lysozyme.

Study Design:

The study has been conducted according to a randomized, double-blind, crossover design.

Study Population: 15 healthy volunteers between 18 and 70 years of age of both genders.

Intervention:

The drinks contained either
  6 g lumiVida™,
  6 g intact lysozyme or
  a combination of 30 mol percent of Trp in the form iVi of lumiVida™ and 70 mol percent of Trp in the form of lysozyme.

Main study endpoints:

$T_{max}$ of the Trp/LNAA—time curve after consumption of the respective study compounds $AUC_{0-240min}$ of plasma Trp after consumption of either lumiVida™, intact lysozyme or the combination $AUC_{0-240min}$ of cysteine, cystine and glutathione after consumption of either lumiVida™ or intact lysozyme $C_{max}$ of cysteine, cystine and glutathione after consumption of either lumiVida™ or intact lysozyme Deign, Population and Treatment Design:

The study followed a randomized, double-blind, crossover design. No placebo was considered necessary, since baseline (t=0) measurements have been taken at each study day. Moreover, the primary research question relates to the comparison of different active treatments.

Population:

15 healthy male or female subjects between 18 and 70 years of age who gave written informed consent.

Exclusion Criteria:

Pregnancy or sexually active women of childbearing potential who are not using a medically accepted contraceptive method Chronic and current illness, at the discretion of the investigator History of psychiatric disorders;

Use of "selective serotonin reuptake inhibitors" (SSRI);

Use of supplements targeting the central nervous system, such as supplements containing tryptophan, ephedrine, or St John's wart Egg allergy Drug abuse Participation in any other study involving investigational or marketed products concomitantly Intolerance to artificial sweeteners Any (history of) gastrointestinal disease that interferes with gastrointestinal function, at the discretion of the investigator Use of medication targeting the gastro-intestinal tract, such as antacids Investigational Product:

The drinks contained either 6 g lumiVida™, 6 g intact lysozyme or a combination of 30 mol percent of Trp in the form of lumiVida™ and 70 mol percent of Trp in the form of lysozyme. The three different conditions were presented as sterile drinks in bottles with straws. All drinks contained 0.10 g sweetener (acesulfame) and were filled up by plain water in order to reach a 300 mL drink volume.

Lysozyme: A hen egg-derived protein. Lysozyme is rich in Trp. It is a naturally occurring food protein that has not been altered in any way. Indeed, lysozyme's total amino acid content makes it a nutritionally very complete protein.

lumiVida™: Hydrolysed lysozyme. lumiVida™ is a hydrolysed form of lysozyme. Hydrolysis of peptides is frequently performed in the food industry to reduce allergenicity (e.g. for infant food formulae), improve application characteristics (e.g. hydrolysates yield clear solutions in water, as opposed to most intact proteins) or facilitate digestion (e.g. for sports nutrition). The hydrolysis involves an enzymatic treatment with food-grade enzymes. As such, hydrolysates have a GRAS-status (Generally Recognised As Safe) in the U.S.A. and are not considered novel foods under the EU food legislation. A product data sheet is attached as FIG. 6.

Study Procedures

The study was done according to a randomized, double-blind, crossover design. Washout periods between treatments were at least three days. No placebo was required since baseline values were obtained before consumption of each product and plasma amino acid levels are not expected to be subject to a placebo effect. The study was composed of four visits. At the first visit after signing the Informed consent form, the eligibility criteria were checked, and appointments were made for the experimental morning sessions.

During three experimental morning sessions, subjects visited the site between 8 and 9 am, having fasted for at least 8 hours. A flexible canula for blood drawings was inserted in their non-dominant forearm. They then ingested one of the experimental drinks. Before and at t=15, 30, 60, 90 120, 180, 210 and 240 minutes after ingestion, blood samples have been taken to measure the effect of the different protein sources on the plasma Trp/LNAA ratio and on some other amino acid concentrations. The intake of any food or drinks other than water was not allowed during these 240 minutes.

Blood samples have been taken by the CRO "Ampha BV", Nijmegen (Ampha BV, Toernooiveld 220, 6525 EC Nijmegen). The amino acid measurements have been performed at DSM Food Specialties according to the internal document method of analysis No C2529. This method describes an HPLC procedure for the determination of amino acids. The principle of the assay is based on chiral separation of amino acids. Fluorescence-based detection is employed.

Plasma Measurements

For Trp and LNAA determination in the blood: Approx. 5 ml blood was collected in a lithium heparin blood tube, swung and put immediately on ice. The sample was subsequently centrifuged and 750 µl plasma was mixed with 5-SSA (4 mg/100 ml plasma). These solutions were centrifuged at 13'000 RPM for 5 minutes and to 20 µl supernatant, 40 µl internal standard was added (160 mg Alpha-amino-adipic acid in 2 litres 1.2 mM HCl). 50 µl Borate buffer (included in Waters AccQ.Tag kit art nr. 186003836), 40 µl 0.4 M NaOH, and 20 µl reagent (included in Waters AccQ.Tag kit art nr. 186003836) were added, mixed, and heated for 10 minutes at 55° C. Subsequently, 1 µl was injected onto the column and the analysis was proceeded as described in Boogers et al. Journal of Chromatography A. 1189 (2008) 406-409.

For cysteine, cystine and glutathione determination in the blood: Blood plasma samples were centrifuged for 10 min at 14'000 RPM. 10 µl blood plasma supernatant was mixed with 90 µl 0.1 N HCl and 100 µl labeled internals standard solution (mix of labeled cysteine ((U-13C3; 15N), CIL, CNLM-3871-PK), cystine (3, 3'-13C), CIL, CLM-520-0) and glutathione ((Glycine-13C2; 15N), CIL, CLM-6245). After mixing, 2 µl was injected on the column.

Statistical Considerations

Descriptive Statistics

Plasma samples from each time point have been analysed for levels of Trp and LNAA, i.e. the sum of Val, Ile, Leu, Tyr, and Phe. The resulting Trp/LNAA ratio was plotted against time post consumption of the intervention product. The differences between the resulting areas under the Trp/LNAA—time curve (Trp/LNAA AUC) of the treatments have been statistically tested.

Plasma samples from each time point have been further analyzed for levels of cysteine, cystine and glutathione. These concentrations were blotted against time post consumption of the intervention product intact lysozyme and lumiVida, but not the mixture. The resulting area under the curve was calculated and statistically compared with the different intervention products. Also $C_{max}$ was calculated and statistically compared with the different intervention products.

Univariate Statistics

The significance of the effect of treatment on $T_{max}$ and AUCs plasma Trp/LNAA—time curves have been assessed using student's t-tests. The parameters cysteine, cystine and glutathione were statistically assessed using the Wilcoxon test with a significance threshold of $p<0.05$.

Results

Trp/LNAA Ratios

Figure 2:
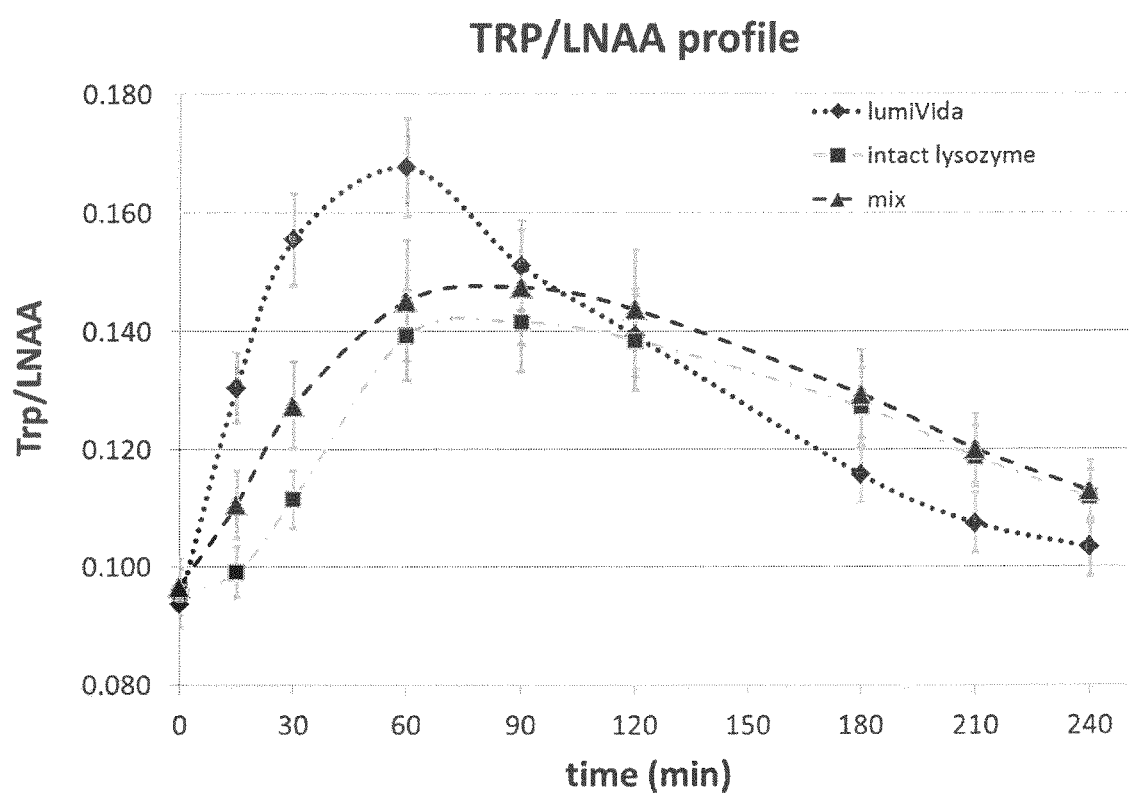
FIG. 2 is a graph showing the kinetics of the plasma Trp/LNAA ratios upon consumption of lumiVida (hydrolysed lysozyme (diamonds)), intact lysozyme (squares), and a mix of intact and hydrolysed lysozyme (triangles). Error bars (standard error) are depicted. All three treatments have similar Trp content.

The plasma Trp/LNAA ratio as a variable of time for the three different treatments is depicted in FIG. 2. All three treatments produced an increase of the Trp/LNAA ratio. The fastest (within 15 minutes) and steepest increase was observed following consumption of the lysozyme hydrolysate (lumiVida™). Intact lysozyme produced a much slower increase of the Trp/LNAA ratio but also the decrease of the Trp/LNAA ratio over time was much slower. The mixture of intact and hydrolysed lysozyme produced an intermediate result. In a "repeated measures" analysis, all three treatments show a significantly different treatment by time interaction ($P<0.001$), indicating that all three curves have significantly different shapes. Noteworthy is that all three products produce similar AUC values indicating that both lysozyme hydrolysate and intact lysozyme are taken up into the blood to a similar extent (Table 1). The dAUC was calculated by subtracting the baseline AUC (baseline*240 min) from the original AUC. lumiVida™ had a significantly higher dAUC than intact lysozyme (Wilcoxon test, p-value 0.0067, FIG. 1). For the original AUC there was no significant difference between lumiVida™ and intact lysozyme

TABLE 1

|  | dAUC | SD |
|---|---|---|
| lumiVida | 9.4 | 2.9 |
| intact lysozyme | 7.3 | 2.9 |
| Mix | 8.4 | 4.2 |

Mean and standard deviation are shown of the baseline-corrected AUC of Trp/LNAA ratios.

Parameters of Other Aminoacids

Figure 3:
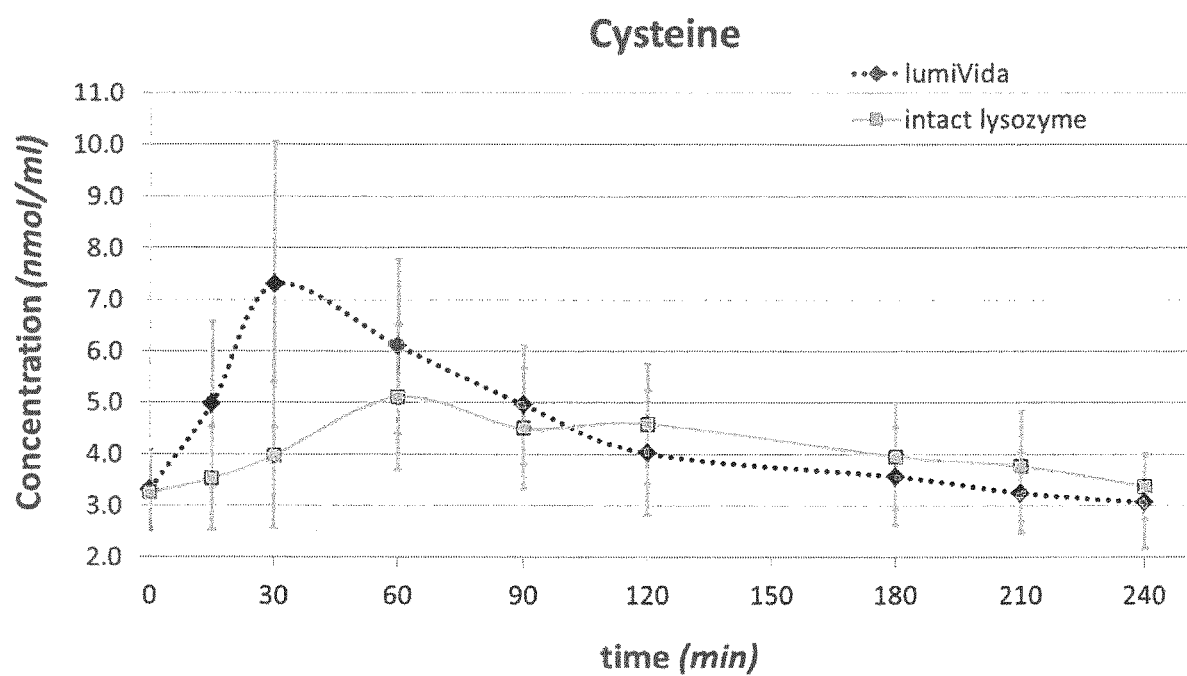
FIG. 3 is a graph showing the kinetics of the plasma cysteine values upon consumption of lumiVida (hydrolyzed lysozyme (diamonds)) or intact lysozyme (squares). Error bars (standard error) are depicted.
Figure 4:
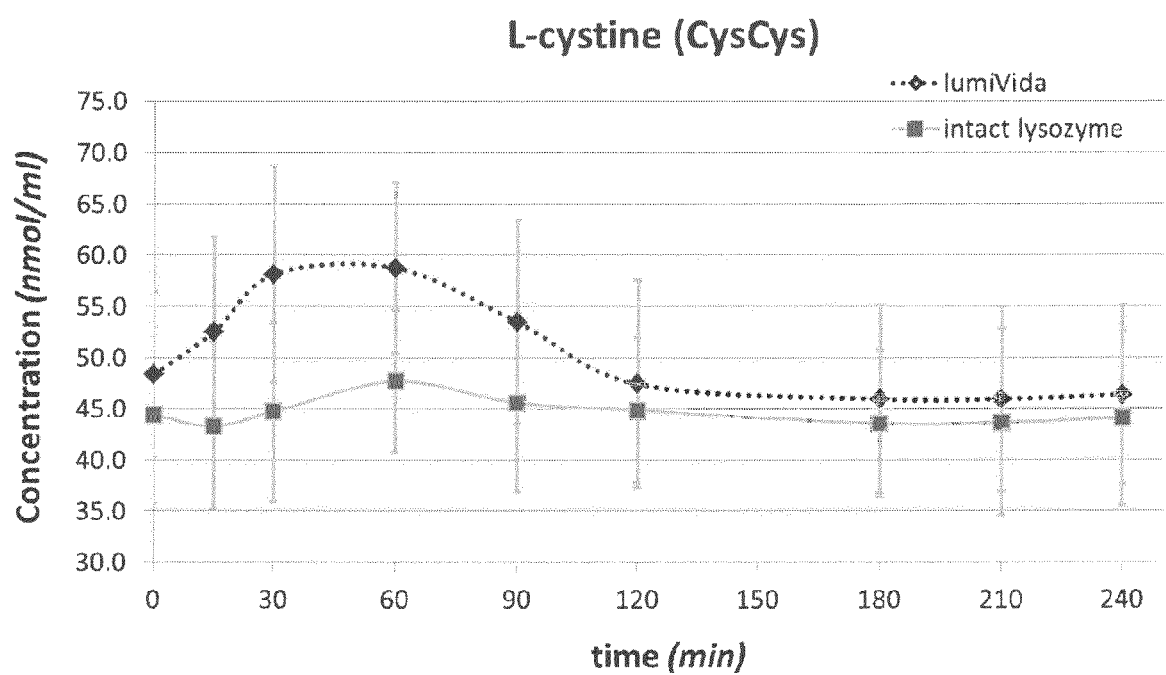
FIG. 4 is a graph showing kinetics of the plasma cystine values upon consumption of lumiVida (hydrolysed lysozyme (diamonds)) or intact lysozyme (squares). Error bars (standard error) are depicted.
Figure 5:
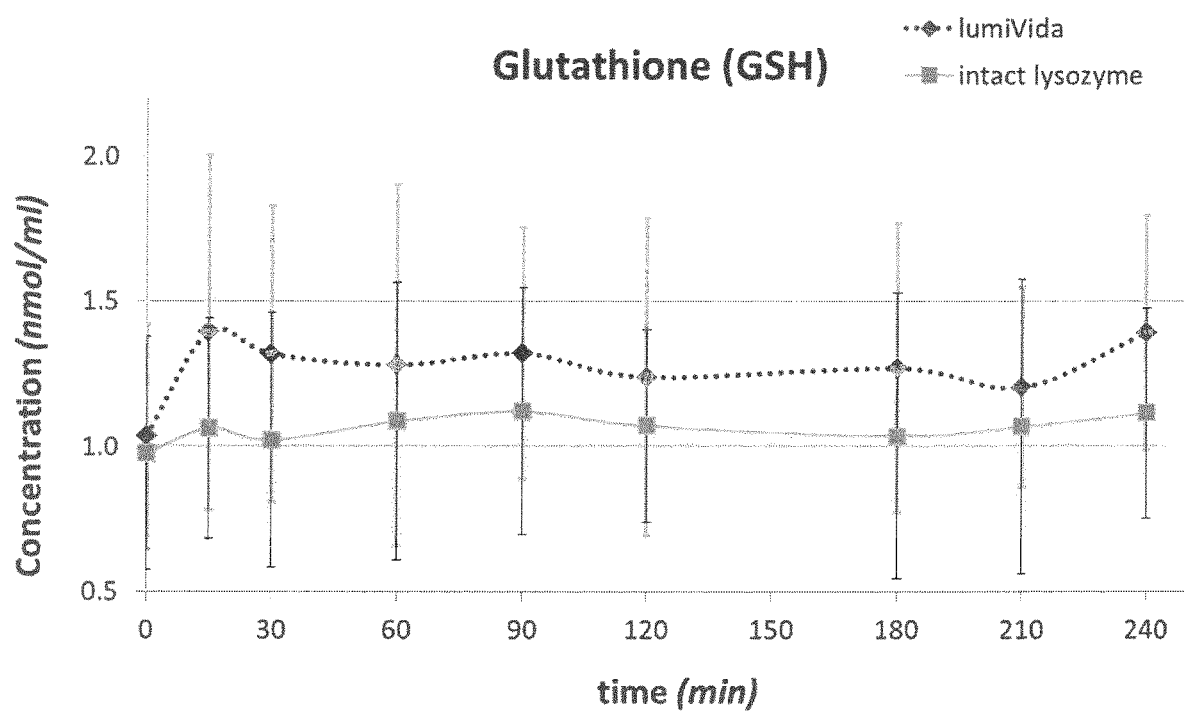
FIG. 5 shows the kinetics of the plasma glutathione values upon consumption of lumiVida (hydrolysed lysozyme (diamonds)) or intact lysozyme (squares). Error bars (standard error) are depicted.
Figure 7A:
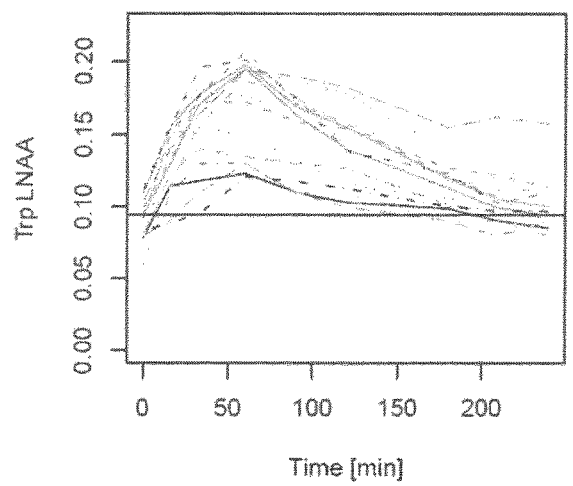
FIGS. 7A and 7B are time curves of the changes in Trp/LNAA ratios after either LumiVida (7A) or intact lysozyme (7B) intake for each individual. In both graphs, individuals are depicted in the same style.
Figure 7B:
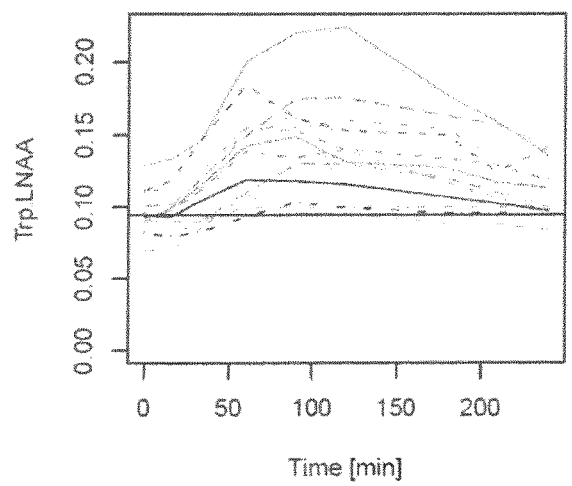
Figure 8A:
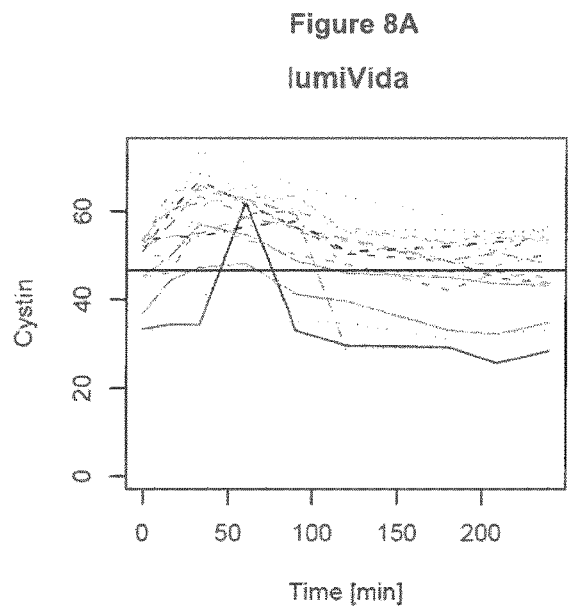
FIGS. 8A and 8B are time curves of changes in either cystine or cysteine plasma concentrations after either lumiVida (8A, 8C) or intact lysozyme (8B, 8D) intake for each individual. In both graphs, individuals are depicted in the same style.
Figure 8B:
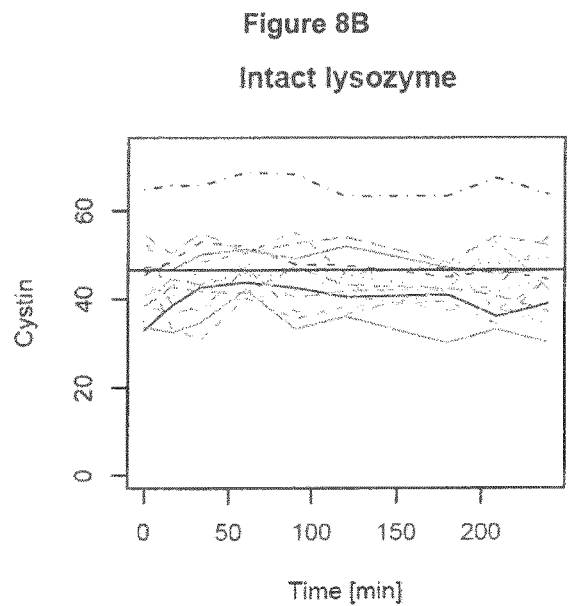
Figure 8C:
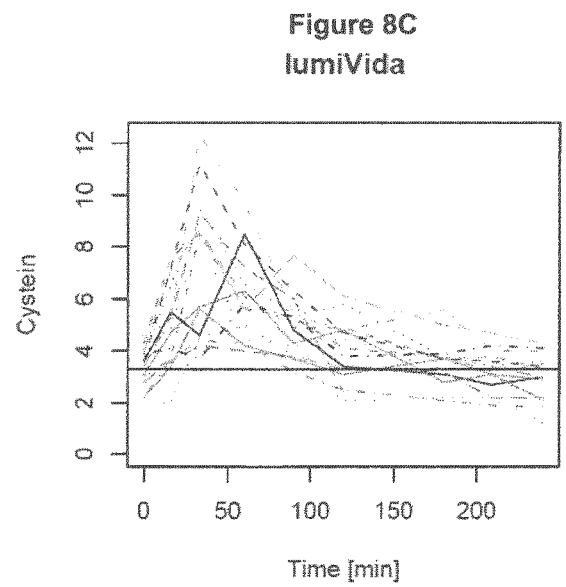
Figure 8D:
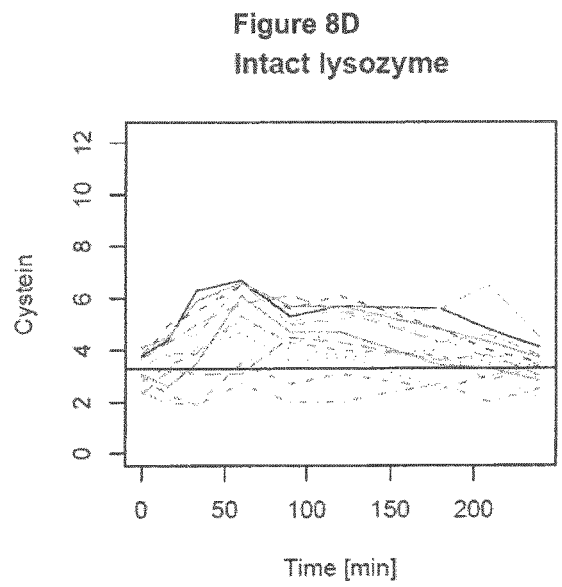
Figure 9A:
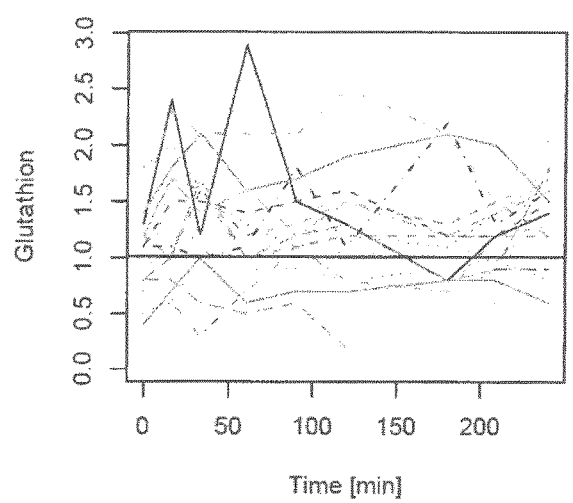
FIGS. 9A and 9B are time curves of changes for glutathione plasma concentrations after either lumiVida (9A) or intact lysozyme (9B) intake for each individual. In both graphs, individuals are depicted in the same style.
Figure 9B:
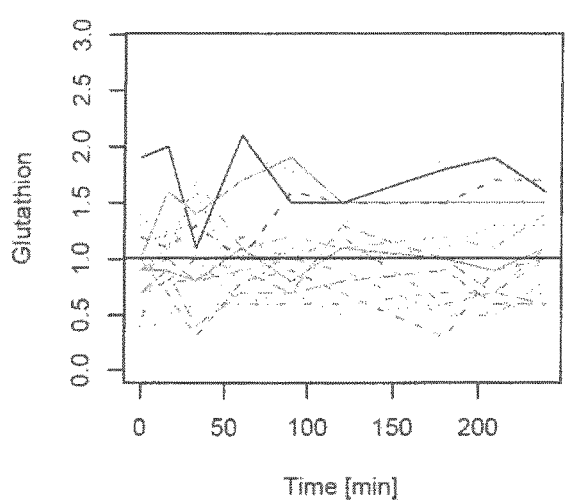
Figure 10A:
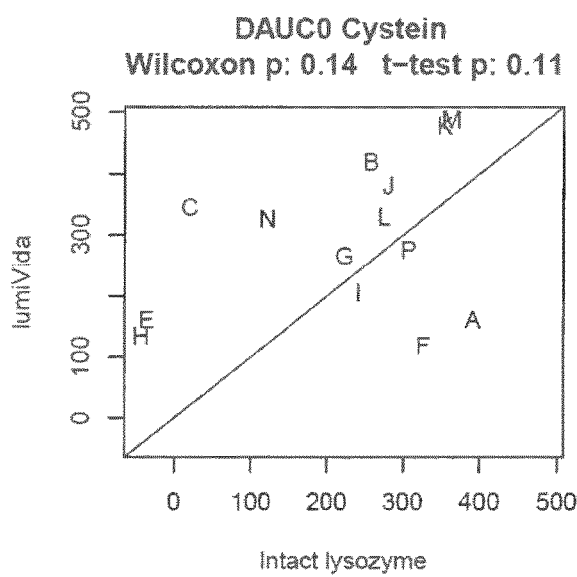
FIGS. 10A and 10B shows the individual dAUC values (corrected for baseline values) of lumiVida versus intact lysozyme are shown for cysteine (cysteine, 10A) and cystine (cystin, 10B) concentrations. Points on the diagonal correspond to equal values in both. Points above the diagonal represent individuals with higher response for lumiVida™ than for intact lysozyme. Overall, the dAUCs were not significantly higher for lumiVida than intact lysozyme dAUC.
Figure 10B:
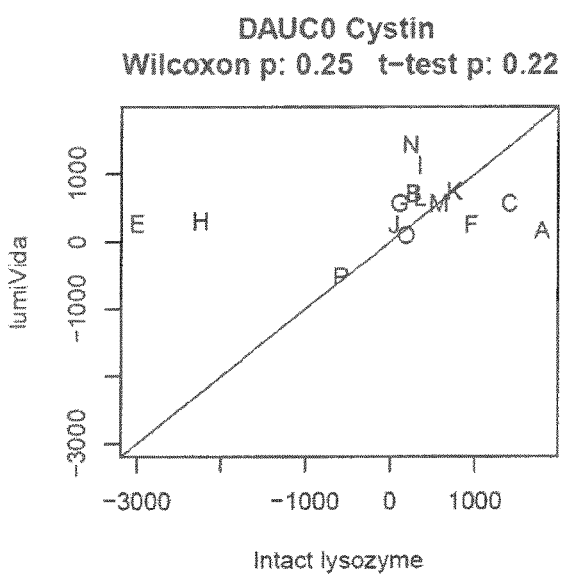
Figure 11A:
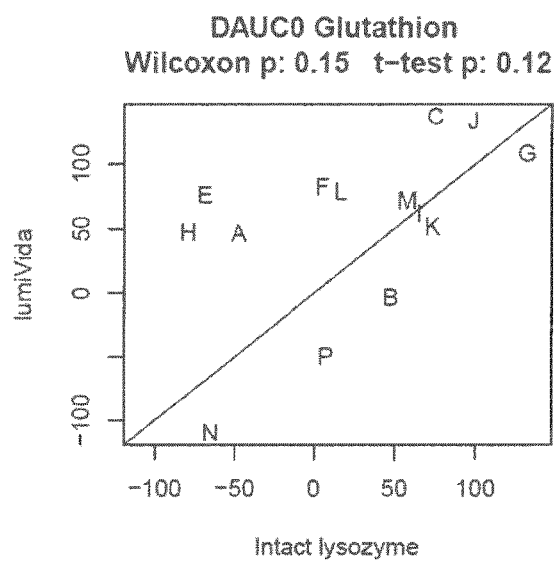
FIGS. 11A and 11B are the individual dAUC values (corrected for baseline values) of lumiVida versus intact lysozyme are shown for glutathione concentrations (left panel, 11A) and for Trp/LNAA ratios (right panel, 11B). Points on the diagonal correspond to equal values in both. Points above the diagonal represent individuals with higher response for lumiVida™ than for intact lysozyme. Overall, the dAUC of glutathione was not significantly higher for lumiVida than intact lysozyme dAUC, however, the dAUC of Trp/LNAA ratio with lumiVida was significantly higher than with intact lysozyme.
Figure 11B:
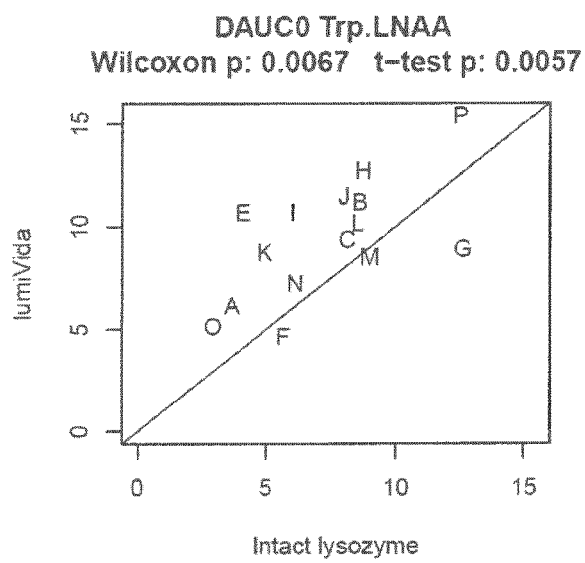
Figure 12A:
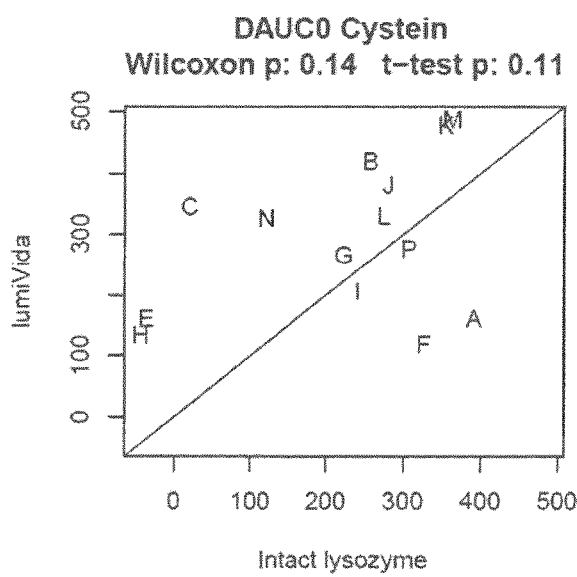
FIGS. 12A and 12B show the individual AUC values (not corrected) of lumiVida versus intact lysozyme for cysteine (12A) and cystine (12B) concentrations. Points on the diagonal correspond to equal values in both. Points above the diagonal represent individuals with higher response for lumiVida™ than for intact lysozyme. Overall, the AUCs were not significantly higher for lumiVida than intact lysozyme AUC, however the cystine AUC was nearly significant in the Wilcoxon test.
Figure 12B:
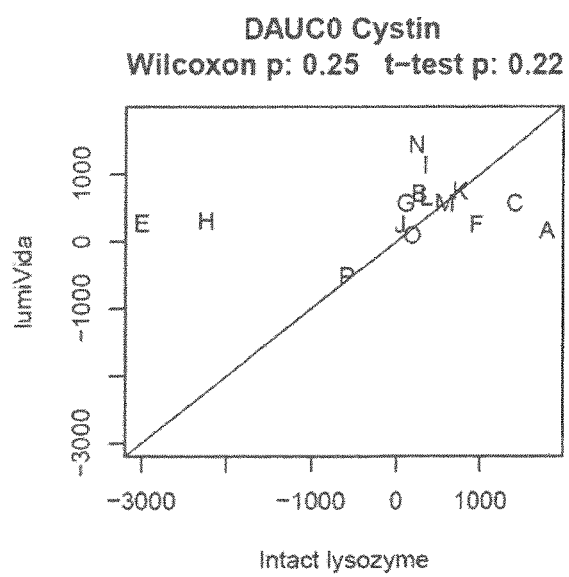
Figure 13A:
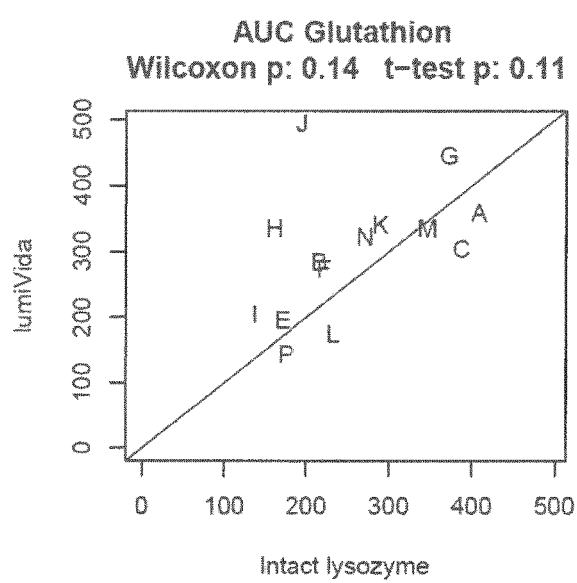
FIGS. 13A and B show the individual AUC values (not corrected) of lumiVida (13A) versus intact lysozyme (13B) for glutathione concentrations and Trp/LNAA ratios. Points on the diagonal correspond to equal values in both. Points above the diagonal represent individuals with higher response for lumiVida™ than for intact lysozyme. Overall, the AUCs were not significantly higher for lumiVida than intact lysozyme AUC.
Figure 13B:
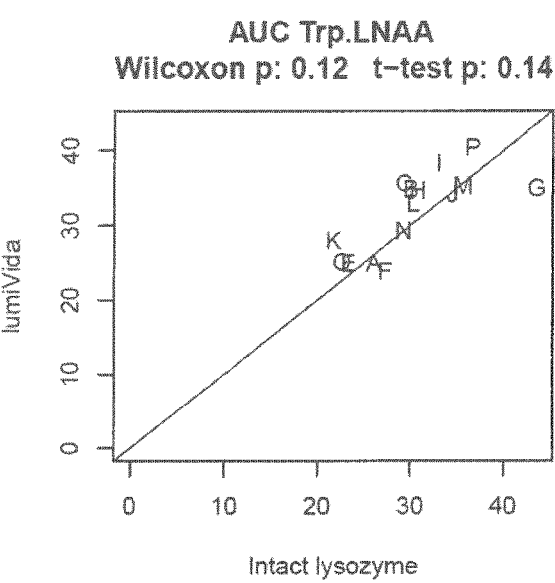
Figure 14A:
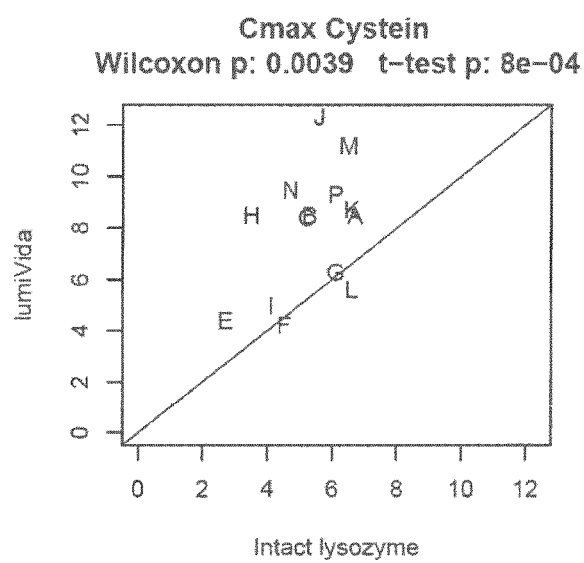
FIGS. 14A and B show the individual Cmax values of lumiVida versus intact lysozyme for cysteine (14A) and cystine (14B) concentrations. Points on the diagonal correspond to equal values in both. Points above the diagonal represent individuals with higher response for lumiVida™ than for intact lysozyme. Overall, both Cmax were significantly higher for lumiVida than intact lysozyme Cmax.
Figure 14B:
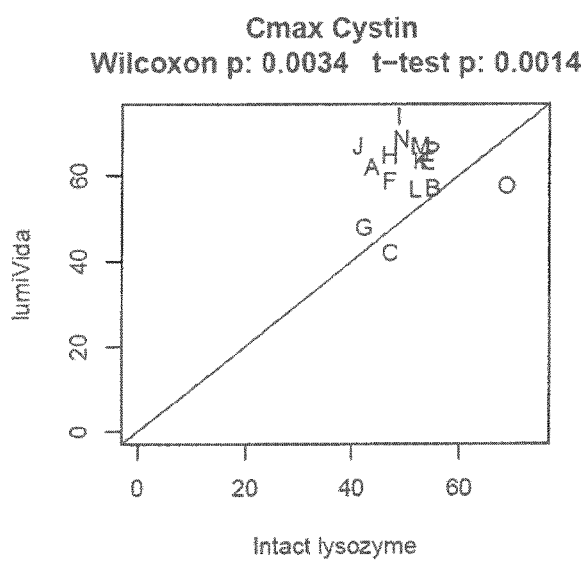
Figure 15A:
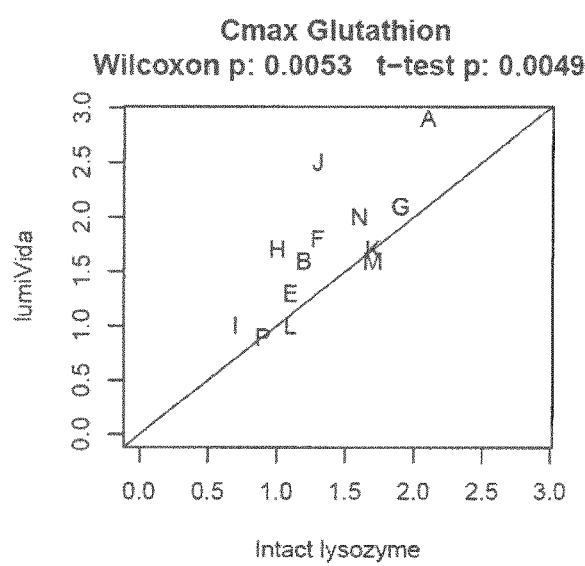
FIGS. 15A and B show the individual Cmax values of lumiVida versus intact lysozyme for glutathione (left pane; 15A) and the Trp/LNAA ratios (right panel; 15B). Points on the diagonal correspond to equal values in both. Points above the diagonal represent individuals with higher response for lumiVida™ than for intact lysozyme. Overall, the both Cmax values were significantly higher for lumiVida than intact lysozyme Cmax.
Figure 15B:
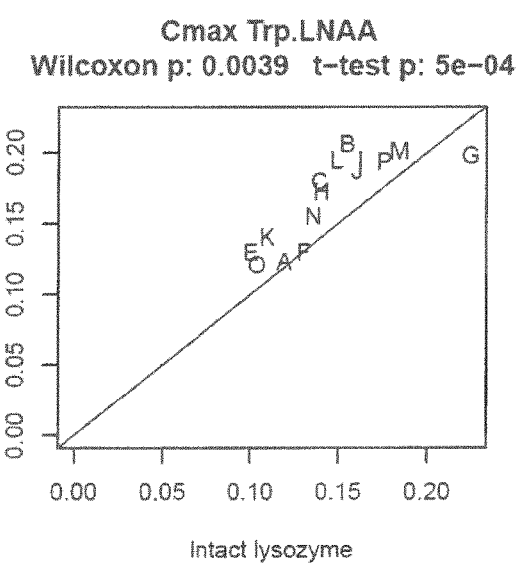

The plasma levels of cysteine, cystine and glutathione as a time course for the lumiVida™ and the intact lysozyme are depicted in FIG. 3, FIG. 4, and FIG. 5. The parameters were statistically assessed using the Wilcoxon test with a significance threshold of p<0.05. The baseline values did not differ significantly between the intact lysozyme and the lumiVida™ treatment for cysteine, cystine and glutathione (Table 2, below). The area under the curve from 0 to 240 minutes did not differ significantly between the treatments, although numerically, all three parameters were higher in lumiVida™ (Table 2, below). $C_{max}$ was significantly higher for lumiVida™ compared to lysozyme in all three parameters (cysteine p=0.0039, cystine p=0.0034 and glutathione p=0,0053) (Table 2). The kinetic profile increased more quickly with lumiVida™ than with lysozyme, resulting in the higher $C_{max}$. The original data is summarized in FIGS. 7-15.

Discussion

In this study we provide data that intake of the lysozyme hydrolysate lumiVida™ is more beneficial in raising Trp/LNAA ratios than the intact protein. We could demonstrate that the increase of this ratio in the blood plasma is bigger (higher Cmax values with lumiVida™ than with the intact lysozyme). Further also the baseline corrected AUCs, which take into account of the daily (individual) variation of the baseline) were bigger after the intake of lumiVida™ than after the intact lysozyme. These findings indicate that the Trp from the hydrolyzed protein lumiVida™ can be more rapidly taken up into the blood system and to a higher extent than with the intact lysozyme. As lumiVida™ and intact lysozyme contain the same amount of Trp, it might be expected that the expose of Trp in the blood system would be similar. However, as our data show that the dAUCs are higher with lumiVida™ than with the intact lysozyme, some Trp from the intact lysozyme will not enter the blood system. As it takes more time to digest the intact lysozyme, the hydrolyzed fragments might get taken up by gut bacteria and therefore might not be available to the blood system anymore. The mixture of lumiVida™ with intact lysozyme got an intermediate response.

Another finding was the significant increase of Cmax plasma values of cysteine, cystine and glutathione after lumiVida™ intake. These increases also mirror the significant increase of the Trp/LNAA ratios reported above. The plasma AUCs of these amino acids were very similar and were not statistically significantly different after lumiVida™ and intact lysozyme intake. This reflects that the amino acids are taken up into the blood quicker after the hydrolysate lumiVida™ than after the intake of intact lysozyme. However the total amino acids exposure to the blood is similar with both compounds, as the AUC is similar. Assuming that efficacy is dependent on reaching a minimal threshold level of a certain amino acid in the blood to start its effect, than the intake of lumiVida™ is expected to be more beneficial than intake of the intact lysozyme.

TABLE 2

|  | Parameter (average) | lumiVida | lysozyme |
|---|---|---|---|
| Cysteine | $C_{max}$ (SD) | 7.8 (2.4)* | 5.3 (1.3)* |
|  | Baseline value (SD) | 3.3 (0.8) | 3.3 (0.7) |
|  | AUC (SD) | 1073.3 (249.0) | 999.7 (244.4) |
|  | N | 15 | 14 |
| Cystine | $C_{max}$ (SD) | 61.0 (8.1)* | 50.4 (6.7)* |
|  | Baseline value (SD) | 48.3 (8.1) | 44.4 (8.6) |
|  | AUC (SD) | 12082.9 (2019.2) | 10726.7 (1769.1) |
|  | N | 15 | 15 |
| Glutathione | $C_{max}$ (SD) | 1.8 (0.6)* | 1.4 (0.4)* |
|  | Baseline value (SD) | 1.0 (0.4) | 1.0 (0.4) |
|  | AUC (SD) | 304.0 (96.0) | 255.7 (90.8) |
|  | N | 15 | 14 |

Average values of $C_{max}$, baseline vales and AUC are indicated for cysteine, cystine and glutathione.
*p-value < 0.05

The invention claimed is:

1. A method of enhancing growth, appearance, and/or volume of keratin-containing tissue comprising orally administering a skin-, hair- or nails-enhancing amount of lysozyme hydrolysate as a tryptophan-containing peptide to a person or animal in need of, or desirous of, enhancing skin, hair or nails such that the person or animal receives 10-100 mg tryptophan (Trp) per day.

2. The method according to claim 1, wherein the method comprises orally administering the lysozyme hydrolysate in an amount from 0.5 grams to 7.5 grams per day.

3. The method according to claim 2, wherein the lysozyme hydrolysate is orally administered in an amount from 1 gram to about 6 grams per day.

* * * * *